United States Patent [19]

Hüsler et al.

[11] Patent Number: 4,950,795

[45] Date of Patent: Aug. 21, 1990

[54] OLIGOMERIC BENZIL KETALS AND THEIR USE AS PHOTOINITIATORS

[75] Inventors: Rinaldo Hüsler; Rudolf Kirchmayr, both of Marly; Werner Rutsch, Fribourg; Manfred Rembold, Aesch, all of Switzerland

[73] Assignee: Ciba-Geigy Corporation, Ardsley, N.Y.

[21] Appl. No.: 233,399

[22] Filed: Aug. 18, 1988

[30] Foreign Application Priority Data

Aug. 27, 1987 [CH] Switzerland ......................... 3285/87

[51] Int. Cl.$^5$ .......................................... C07C 49/213
[52] U.S. Cl. ................................... 568/331; 564/342; 564/443; 564/219; 564/220; 564/185; 544/220; 568/43
[58] Field of Search .................. 568/331, 43; 528/220; 564/342, 443, 219, 220; 544/220

[56] References Cited

U.S. PATENT DOCUMENTS

| | | | |
|---|---|---|---|
| 3,715,293 | 2/1973 | Sandner et al. | 204/159.14 |
| 3,878,169 | 4/1975 | Guillet et al. | 528/220 |
| 3,978,133 | 8/1976 | Reister et al. | 568/331 |
| 3,998,712 | 12/1976 | Hickmann et al. | 204/159.15 |
| 4,144,156 | 3/1979 | Kuesters et al. | 568/331 |
| 4,190,602 | 2/1980 | Brunesholz et al. | 260/590 |
| 4,672,079 | 6/1987 | Li Bassi et al. | 522/35 |

FOREIGN PATENT DOCUMENTS 3534645  4/1987  Fed. Rep. of Germany ......................... 204/159.15

*Primary Examiner*—James H. Reamer
*Attorney, Agent, or Firm*—Stephen V. O'Brien

[57] ABSTRACT

Compounds of the formula I

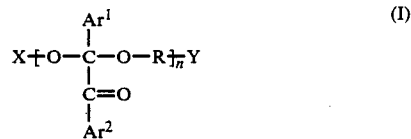

in which n is 1-30 and X, Y, R, Ar$^1$ and Ar$^2$ are as defined in claim 1 can be prepared by reaction of a benzil dialkyl ketal with a diol. Depending on the molar ratio of the two reaction components, products having a different polycondensation degree n are obtained. The compounds can be used as photoinitiators.

3 Claims, No Drawings

OLIGOMERIC BENZIL KETALS AND THEIR USE AS PHOTOINITIATORS

The present invention relates to oligomeric benzil ketals, a process for their preparation and photocurable compositions containing these benzil ketals as photoinitiators.

Photopolymerization of unsaturated compounds has acquired at the present time great importance for various industrial branches, thus, for example, for coatings, for printing inks, for the preparation of photoresists and other applications in electronics. For this reaction, photoinitiators which accelerate the polymerization and thus the curing of the substrate are added to the substrates to be polymerized. These initiators and their cleavage products remain in the cured substrate after the photopolymerization and can migrate to the surface of the substrate. In certain cases, this can lead to health hazards, for example in coverings of food packages. This can also result in odour nuisances, for example in the case of protective coatings for books or gramophone record jackets.

To prevent migration and evaporation, the use of polymeric photoinitiators has also already been proposed. Thus, EP-A-161,463 describes the use of polymers of the formula

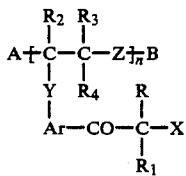

in which X is OH, $NH_2$, SH or a derivative of these groups or is halogen, SCN or $N_3$, Ar is an arylene radical and n is 2 to $10^6$. The preparation of these products is relatively complicated and their effect as photoinitiators is unsatisfactory for many applications.

In DE-A-3,534,645, the use of acrylically unsaturated photoinitiators is described which can copolymerize with the substrate during the photopolymerization. However, the storage life of these initiators is limited.

A novel class of oligomeric to polymeric photoinitiators has now been found which are polyketals of aromatic 1,2-diketones. Monoketals of aromatic 1,2-diketones (benzil ketals) are known as effective photoinitiators, for example from US-A-3,715,293, DE-A-2,232,365 and DE-A-2,337,813 and are used as such in industry. Compared with these monomeric benzil ketals, the polyketals according to the invention have the advantage of less tendency to migrate, lower extractability, less odour nuisance and less yellowing of the photopolymerized substrate.

The invention relates to polyketals of the general formula I and mixtures thereof,

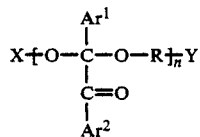

in which X is a group $R^1$ or HO—R—, Y is a group —OH or

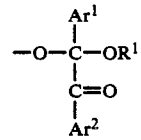

n has a value from 1 to 30, $Ar^1$ and $Ar^2$ independently of one another are phenyl or phenyl substituted by $C_1$-$C_4$alkyl, $C_1$-$C_4$alkoxy or halogen, R is a divalent radical and is either (a) a $C_4$-$C_{50}$polymethylene radical which can be interrupted once or several times by —O—, —S—, —SO—, —$SO_2$—, —CO—, —CONH—, —$N(R^2)$—, —O—$Si(R^3)(R^4)$—O— or by one or more carbocyclic or heterocyclic rings, and which can be mono- or polysubstituted by $C_1$-$C_{18}$alkyl, $C_3$-$C_5$alkenyl, $C_5$-$C_6$cycloalkyl, phenyl, halogen, cyano, hydroxyl, $C_1$-$C_{12}$alkoxy, $C_1$-$C_{12}$-alkylthio, phenoxy, $C_2$-$C_{12}$alkanoyloxy, benzoyloxy, $C_2$-$C_5$alkoxycarbonyl, $C_2$-$C_8$dialkylamino, morpholino, piperidino, trimethylsiloxy or by one of the groups $+O-C(Ar^1)$ $(-CO-Ar^2)-O-R+_{n'}Y$, $-(C_1-C_4$—alkylene)—$R^6$, —O—$CH_2CH_2$—$R^6$, —O—$CH_2$—$CH(CH_3)$—$R^6$ or —S—$CH_2CH_2$—$R^6$, where n' is smaller than n and has a value from 0 to 29, or (b) is a $C_4$-$C_8$alkenylene or alkynylene radical or (c) is a divalent cycloaliphatic radical having 6-20 C atoms or (d) is a —$CH_2$—Z—$CH_2$— radical, in which Z is a divalent cycloaliphatic, aromatic or heterocyclic radical having 4–15 C atoms, $R^1$ is $C_1$-$C_4$alkyl, $R^2$ is hydrogen, $C_1$-$C_4$alkyl, cyclohexyl, phenyl, chlorophenyl, tolyl, benzyl, $C_2$-$C_5$alkanoyl, benzoyl, toluyl or is a —$SO_2$—$R^5$, —$CH_2C$-$H_2$—$R^6$ or —$CH_2$—$CH(CH_3)$—$R^6$ group, $R^3$ and $R^4$ independently of one another are methyl or phenyl, $R^5$ is $C_1$-$C_{16}$alkyl, phenyl or $C_7$-$C_{20}$alkylphenyl and $R^6$ is hydroxyl, $C_1$-$C_4$alkoxy, $C_2$-$C_4$alkanoyloxy or $+O-C-(Ar^1)(-CO-Ar^2)-O+$.

$Ar^1$ and $Ar^2$ as substituted phenyl can be, for example, 4-tolyl, 2-tolyl, 4-tert-butylphenyl, 2-methoxyphenyl, 4-methoxyphenyl, 4-ethoxyphenyl, 4-isopropoxyphenyl, 4-chlorophenyl, 4-bromophenyl or 4-fluorophenyl. Preferably $Ar^1$ and $Ar^2$ are phenyl. $R^1$ and $R^2$ as $C_1$-$C_4$—alkyl can be, for example, methyl, ethyl, propyl, isopropyl, n-butyl or isobutyl. Preferably $R^1$ is methyl.

R is a divalent radical formed by the removal of the two hydroxyl groups from a diol. Suitable diols will be listed later. The ring of a polymethylene radical R which is interrupted by one or more carbocyclic or heterocyclic rings can be 5- to 8-membered and contain 3–8 C atoms, 1–3 N atoms, 1–3 0 atoms and/or 1–2 S atoms. A cycloaliphatic radical R can be mononuclear or binuclear and contain 5–20 C atoms. A cycloaliphatic, aromatic or heterocyclic radical Z can be mononuclear or binuclear, contain 4–15 C atoms, 1–3 N atoms, 1–2 0 atoms and/or 1–2 S atoms and the individual rings can be 5- to 8-membered.

R2 as $C_2$-$C_5$alkanoyl can be, for example, acetyl, propionyl, butyryl, isobutyryl or valeryl.

$R^5$ as $C_1$-$C_{16}$alkyl can be, for example, methyl, ethyl, propyl, butyl, tert-butyl, hexyl, octyl, decyl, dodecyl or hexadecyl. $R^5$ as $C_7$-$C_{20}$alkylphenyl can be, for example, 4-tolyl, 4-butylphenyl, 4-octylphenyl, 4-dodecylphenyl or 4-tetradecylphenyl.

Where the invention relates to an individual compound of the formula I, the index n is a whole number. In most cases, however, it relates to mixtures of compounds having different n's and in these mixtures n is an average value which, in most cases, is not a whole number.

Preferably, polyketals of the formula I are those in which n is 2-20, $Ar^1$ and $Ar^2$ independently of one another are phenyl, tolyl, chlorophenyl or bromophenyl, R is a polymethylene radical having 4-30 C atoms which can be interrupted once or several times by —O—, —S—, —N($R^2$)— or by a group

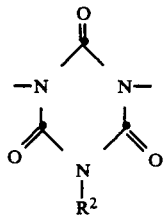

and which can be mono- or polysubstituted by $C_1$-$C_4$alkyl, cyclohexyl, phenyl, halogen, $C_1$-$C_4$alkoxy, phenoxy, $C_7$-$C_9$phenylalkyl, $C_2$-$C_8$dialkylamino, morpholino or piperidino, $R^1$ is methyl or ethyl, $R^2$ is hydrogen, $C_1$-$C_4$alkyl, cyclohexyl, phenyl, tolyl, benzyl, acetyl, benzoyl or is a group —$CH_2CH_2R^6$ or —$SO_2$—$R^5$, $R^5$ is $C_1$-$C_{12}$alkyl, phenyl or $C_7$-$C_{18}$alkylphenyl, $R^6$ is hydroxy or -[O—C($Ar^1$)(—CO—$Ar^2$)—O-] X and Y are as defined above.

Particularly preferably, polyketals of the formula I are those in which n is 2-10, $Ar^1$ and $Ar^2$ are phenyl, R is either a —($CH_2$)m— radical having an m of 5-10 or is a —($CH_2CH_2O$)p$CH_2CH_2$— radical having a p of 1-14 or is a —$CH_2CH_2$—N($R^2$)—$CH_2CH_2$- radical, $R^1$ is methyl, $R^2$ is $C_1$-$C_4$alkyl, cyclohexyl, phenyl or benzyl and X and Y are as defined above, and in particular polyketals of the formula I are those in which n is 2-10, $Ar^1$ and $Ar^2$ are phenyl, R is a —($CH_2CH_2O$)p$CH_2CH_2$— radical having a p of 1-10 or is a —($CH_2$)$_6$— radical and $R^1$ is methyl.

The polyketals according to the invention can be prepared by transketalization of benzil dialkyl ketals of the formula II with diols of the formula III:

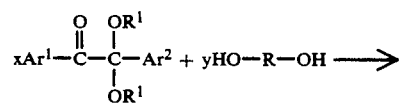

(II)    (III)

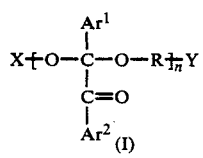

(I)

the molar ratio of the components x:y being in the range from 0.5 to 2. A molar ratio x:y of close to 0.5 gives polyketals having a low n and hydroxyl terminal groups (X=HO—R—, Y=—OH). A molar ratio x:y of 1 or close to 1 gives polyketals which have not only hydroxyl but also ketal terminal groups. A molar ratio x:y close to 2 gives polyketals having predominantly ketal terminal groups (X=$R^1$, Y=—O—C($Ar^1$)(CO$Ar^2$)—$OR^1$). It is therefore possible, by varying the molar ratios, to vary the properties of the product. The molecular weight and thus the properties of the products can also be varied by means of the reaction times.

The dialkyl ketals of the formula II used as the starting material are known compounds and described, for example, in US—A—3,715,293, DE-A-2,232,365 and DE-A-2,337,813. Benzil dimethyl ketal and benzil diethyl ketal are commercially available.

The diols of the formula III required as the starting materials are also known compounds. Many of them are commercially available. They can also be mixtures of technical grade. Examples of diols of the formula III usable according to the invention are: butane-1,4-diol, pentane-1,5-diol, hexane-1,6-diol, heptane-1,7-diol, octane-1,8-diol, nonane-1,9-diol, decane-1,10-diol, dodecane-1,12-diol, 3-methylpentane-1,5-diol, pentane-1,4-diol, hexane-2,5-diol, 2-trans-butene-1,4-diol, 2-butyne-1,4-diol, 3-hexyne-2,5-diol, cyclohexane-1,3-diol and cyclohexane-1,4-diol, cyclopentane-1,3-diol, cyclooctane-1,5-diol and cyclooctane-1,4-diol, decahydronaphthalene-1,4-diol and decahydronaphthalene-1,5-diol, dicyclohexyl-4,4'-diol, 1,2- and 1,4-bis(hydroxymethyl)-cyclohexene, 1,3- and 1,4-bis(hydroxymethyl)benzene, 1,4-bis(hydroxymethyl)-2,3,5,6-tetramethylbenzene, 2,5-bis(hydroxymethyl)furan, 2,5-bis(hydroxymethyl)-tetrahydrofuran, 1,4-bis(2-hydroxyethoxy)benzene, diethylene glycol, triethylene glycol and tetraethylene glycol, polyethylene glycol having a molecular weight of 200, 300, 400, 600, 1,000 or 1,500, dipropylene glycol and tripropylene glycol, polypropylene glycol having a molecular weight of 400, 750 or 1,200, poly(tetramethylene) glycol having a molecular weight of 650 or 1,000, 3,8-dioxadecane-1,10-diol, 4,10-dioxadecane-2,11-diol, 5-oxanonane-3,7-diol, isopropylidene-4,4' dicyclohexanol, 2,2-bis[4-(2- hydroxyethoxy)-phenyl]-propane, 2,2-bis[4-(2-hydroxypropoxy)phenyl] propane, bis(2-hydroxyethyl) terephthalate, bis(2-hydroxyethyl)-terephthalamide, 3-thiapentane-1,5-diol, 4-thiaheptane-1,7-diol, 3,6-dithiaoctane-1,8-diol, diethanolamine, N-methyldiethanolamine, N-butyldiethanolamine, N-tert-butyldiethanolamine, N-cyclohexyldiethanolamine, N,N-bis(2-hydroxyethyl)aniline, N,N-bis(2-hydroxyethyl)toluidine, N,N-bis(2-hydroxyethyl)-m-chloroaniline, N,N'-bis(2-hydroxyethyl)-1,4-phenylenediamine, N,N'-bis(2-hydroxyethyl)piperazine, bis(2-hydroxypropyl)amine, bis(2-hydroxypropyl)methylamine, N,N'-bis(2-hydroxy-ethyl)ethylenediamine, N,N'-(2-hydroxyethyl)-trimethylenediamine, N,N-bis(2-hydroxyethyl)acetamide, N,N-bis(2-hydroxyethyl)benzamide, N,N-bis(2-hydroxyethyl)toluenesulfonamide, N,N-bis(2-hydroxyethyl)benzenesulfonamide or N,N-bis(2-hydroxyethyl)methanesulfonamide.

It is also possible to use mixtures of several diols or mixtures of diols with those triols or polyols which do not form cyclic ketals. Examples of triols and tetrols which are also usable are tris(hydroxyalkyl)benzenes, for example 1,3,5-tris(hydroxymethyl)benzene, 1,3,5-tris(2-hydroxyethyl)benzene or 1,3,5-tris(4-hydroxybutyl)benzene; tris(hydroxyalkyl)cyclohexane, for example 1,3,5-tris(hydroxymethyl)cyclohexane, 1,3,5-tris(3-hydroxypropyl)cyclohexane or 1,3,5-tris(8-hydroxyoctyl)cyclohexane; 3-(2-hydroxyethyl)pentane-1,5-diol; 3-(2-hydroxyethyl)-3-methylpentane-1,5-diol; 3,3-bis(2-hydroxyethyl)pentane-1,5-diol; 4,4-bis(3-hydroxypropyl)heptane-1,5-diol; tris(2-hydroxyethyl) isocyanurate; triethanolamine; tris(2-hydroxypropyl)amine or N,N,N',N'-tetrakis(2-hydroxyethyl)ethylenediamine.

The transketalization is catalysed by acids. These acids can be either proton acids or Lewis acids. Examples of these are HCl, $H_2SO_4$, $H_3PO_4$, $CH_{SO_3}H$, $CH_3\text{-}C_6H_4SO_3H$, $CF_3COOH$, $BF_3$ or $AlCl_3$. Basic diols or triols are neutralized with an acid before the reaction.

The reaction can be carried out in an inert solvent, for example benzene, xylene or chlorobenzene, although it is preferably carried out without a solvent. The alcohol RIOH formed in the transketalization can be distilled off and indicates the progress of the reaction.

The reaction can be completed by heating. Preferably, it is heated to 60°-130°C., in particular to 70°-90° C. Once the reaction is finished, the catalyst is removed, for example by distillation or by neutralization with a base. The crude product thus obtained can be used without further purification for most purposes. The products (polyketals) are viscous liquid materials or low-melting resin-like solids and are readily soluble in organic solvents.

A second method of preparing the compounds of the formula I is the direct ketalization of aromatic 1,1-diketones of the formula IV with the diols of the formula III:

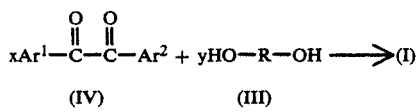

In this case, too, the molecular weight and the terminal groups of the products can be varied within wide limits by the molar ratio x:y. In this case, too, acids are used as catalysts and the reaction is preferably carried out without a solvent. Preferably, the reaction is carried out at 0° to 120° C., in particular at 0° to 80° C. The water formed in the reaction can be removed by the addition of a dehydrating agent. A special variation of this process is carrying out the reaction in the presence of at least molar amounts of thionyl chloride analogously to the process of DE-B-2,337,813.

By the above process, mixtures of compounds of the formula I having a different n are usually obtained. These mixtures are usually used as such (see below). However, the individual components can also be obtained in pure form by conventional physical separation methods, for example by chromatographic methods.

The products of the formula I can be used as photoinitiators for the photopolymerization of ethylenically unsaturated compounds. These compounds can be mono- or polyunsaturated compounds and it can be an individual unsaturated compound or a mixture of unsaturated compounds.

Examples of monounsaturated compounds are acrylates or methacrylates of monohydric alcohols, acrylamides and similar acrylic acid derivatives, for example methyl, ethyl, butyl, isooctyl or hydroxyethyl acrylate, methyl or ethyl methacrylate, acrylonitrile, acrylamide, N-butyl(methacrylamide); and also vinyl and allyl compounds, for example vinyl acetate, vinyl stearate, N-vinylpyrrolidone, vinylidene chloride, styrene or allyl acetate.

Examples of polyunsaturated compounds are acrylates, methacrylates or itaconates of polyols, for example ethylene glycol diacrylate, diethylene glycol dimethacrylate, triethylene glycol diacrylate, butane-1,4-diol diacrylate, propane-1,2-diol diacrylate, butane-1,3-diol dimethacrylate, neopentyl glycol diacrylate, trimethylolpropane di(meth)acrylate, trimethylolethane di(meth)acrylate, glycerol diacrylate and glycerol triacrylate, pentaerythritol diacrylate, pentaerythritol triacrylate and pentaerythritol tetraacrylate or pentaerythritol methacrylate, dipentaerythritol tetraacrylate, d pentaerythritol pentaacrylate and dipentaerythritol hexaacrylate or dipentaerythritol methacrylate or dipentaerythritol itaconate, sorbitol tetraacrylate, sorbitol hexamethacrylate, diacrylates or dimethacrylates of cyclohexane-1,4-diol, 1,4-dimethylolcyclohexane, bisphenol A, 2,2-bis(4-hydroxyphenyl)propane of polyethylene glycols or of oligoesters or oligourethanes having terminal hydroxyl groups. Acrylamides can also be used as polyunsaturated monomers, for example methylenebisacrylamide, hexamethylene-1,6-bisacrylamide, diethylenetriaminetrismethacrylamide, bis(methacrylamidopropoxy)ethane or ethyl 2-acrylamidoacrylate. Examples of polyunsaturated vinyl and allyl compounds are divinylbenzene, ethylene glycol divinyl ether, diallyl phthalate, allyl methacrylate, diallyl maleate, triallyl isocyanurate or triallyl phosphate.

Polymeric or oligomeric polyunsaturated compounds, too, can be photopolypolymerized with crosslinking, for example unsaturated polyesters and copolyesters of maleic acid and fumaric acid, (meth)acrylates of polyvinyl alcohol or homopolymers or copolymers of butadiene or isoprene. Further usable polyunsaturated components are the reaction products of polyepoxides with acrylic or me.hacrylic acids. The polyepoxides used are predominantly those commercially available epoxy resin precursors which are available in different molecular weights.

In most cases, mixtures of these unsaturated compounds are used for the photopolymerization in order to be able to vary the properties of the polymers for the desired practical use. Examples of these mixtures are mixtures of diacrylates with polyester acrylates or with polyurethane acrylates, mixtures of mono-, di- and triacrylates, mixtures of unsaturated polyesters of maleic acid with styrene or other mixtures of polymeric/oligomeric unsaturated compounds with di-, tri- or tetraacrylates. These mixtures can consist of two, three or even several unsaturated components.

Photocurable compositions, such as are used for various purposes, in most cases, contain, apart from the photopolymerizable compounds and the photoinitiators, a number of other additives. Thus, it is very common to add thermal inhibitors which, by mixing of the components during the preparation of the mixtures, have the function of protecting them from a premature polymerization. Used for this purpose are, for example, hydroquinone, hydroquinone derivatives, p-methoxyphenol, $\beta$-naphthols or sterically hindered phenols, for example 2,6-di(tert-butyl)-p-cresol. Furthermore, small amounts of UV absorbers can be added, for example those of the benzotriazole, benzophenone or oxalanilide type. Likewise, light stabilizers of the sterically hindered amine type (HALS) can be added.

To increase the storage stability in the dark, copper compounds such as copper naphthenate, copper stearate or copper octanoate, phosphorus compounds such as triphenylphosphine, tributylphosphine, triethyl phosphite, triphenyl phosphite or tribenzyl phosphite, quaternary ammonium compounds such as tetramethylammonium chloride or trimethylbenzylammonium chloride or hydroxylamine derivatives, for example N-diethylhydroxylamine can be added.

The photocurable compositions can also contain polymeric binders which are not unsaturated compounds. Examples of these compounds are polyacrylates, cellulose esters and cellulose ethers, polyvinyl esters, vinyl chloride polymers, polyamides, polyesters, polyethers or styrene/maleic anhydride copolymers Further customary additives are pigments, dyes, fillers, corrosion inhibitors, adhesives, wetting agents or flow-improving agents. For certain applications, solvents can also be added. However, preferably no solvents are used.

Further customary additives are photosensibilizers, which absorb in certain wavelength regions and transfer the energy absorbed to the initiators or function themselves as additional initiators. Examples of these compounds are in particular thioxanthone, anthraquinone and coumarin derivatives.

Further customary additives are accelerators of the amine type, which are of importance in particular in pigmented formulations because they act as chain-transfer agents. Examples of these compounds are N-methyldiethanolamine, triethylamine, ethyl p-dimethylaminobenzoate or Michler's ketone.

Therefore, the invention also relates to photocurable compositions containing at least one ethylenically unsaturated compound and at least 0.5 to 20% by weight, in particular 1–5% by weight, of a compound of the formula I.

The photocurable compositions according to the invention are suitable for use as coating material for substrates of any type, for example wood, paper, ceramics, plastics such as polyester films and cellulose acetate films and metals such as copper and aluminium to which a protective layer or an image is to be applied by photopolymerization.

Photocuring has great importance for printing inks because the drying time of the binder is a decisive factor for the manufacturing speed of graphic products and should be of the order of fractions of seconds.

UV-curable printing inks are of importance in particular for screen printing.

The photocurable mixtures according to the invention are also highly suitable for the manufacture of printing plates. For this purpose, for example, mixtures of soluble linear polyamides or of styrene/butadiene rubber containing photopolymerizable monomers, for example acrylamides, and a photoinitiator are used. Films and plates made from these systems are exposed via the negative (or positive) of the original and the uncured portions are then eluted with a solvent.

Another area of application of photocuring is the metal coating, for example in painting sheets for tubes, cans or bottle stoppers and also the photocuring of plastic coatings, for example of floor or wall coverings based on PVC.

Examples of photocuring of paper coatings are the colourless coating of labels, gramophone record jackets or book jackets.

Another important application of photocuring compositions is that for imaging processes and for the optical production of information carriers. In this process, the layer applied to the carrier is irradiated with light of short wavelength via a photomask and the unexposed parts of the layer are removed by treatment with a solvent (=developer). The exposed parts are cross-linked polymers and therefore insoluble and remain on the carrier. In the presence of appropriate dyes, visible images are produced. Where the carrier i a metallized layer, the metal can be etched away in the unexposed areas after exposing and developing or can be thickened by electroplating. In this manner, printed circuits and photoresists can be produced.

Suitable light sources for exposure are those having a high percentage of light of short wavelength. At the present time, appropriate technical apparatuses and various types of lamps are available for this. Examples are carbon-arc lamps, xenon-arc lamps, mercury vapour lamps, metal halogen lamps, fluorescent lamps, argon incandescent lamps or photographic flood-light lamps. In recent times, laser light sources have also been used. These can be used even without photomasks; in this case, the directed laser beam writes directly on the photocurable layer.

On use as exterior coating, curing by sunlight is also possible.

The Examples which follow illustrate the preparation and the use of the novel initiators. Parts and percentages are by weight, unless otherwise stated.

PREPARATION EXAMPLES

A mixture of 153.8 g (0.6 mole) of benzil dimethyl ketal, 90.1 g (0.6 mole) of triethylene glycol and 3.9 g of toluene-4-sulfonic acid monohydrate are heated to 75–85° C. under an aspirator vacuum (20–30 mbar). At about 63° C., everything is dissolved. The course of the reaction is monitored by thin-layer chromatography. The reaction is stopped as soon as less than 1% of benzil dimethyl ketal is present in the mixture or the amount of benzil formed is larger than the amount of benzil dimethyl ketal still present. This is the case after 2–3 hours. The yellow solution is then cooled and neutralized with 3.8 g of a 30% solution of sodium methylate in methanol. The mixture is then heated to 60° C. under an aspirator vacuum and the methanol is distilled off. The liquid residue is diluted with 500 ml of toluene, stirred with 10 g of activated carbon and filtered through a Hyflo bed. The filtrate is evaporated in vacuo. This gives 208.8 g of a yellow, viscous oil (photoinitiator no. 1).

Analysis of the 100 Mhz $^1$H-NMR spectrum of the product gave a ratio of 5:5:1 for the individual integration areas aromatic A ($\delta$8.3–7.0, 3m, 10H), diol D ($\delta$4.0–3.3, m, 12H) and methoxy M ($\delta$3.2, 2s, 3H). These values correspond approximately to the following average formula:

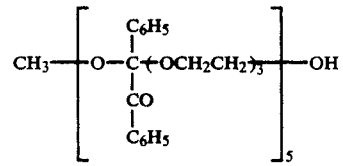

This formula corresponds to an empirical formula $C_{101}H_{114}O_{26}$ having a molecular weight of 1744.

| Elemental analysis: | calculated | C 69.56% | H 6.59% |
|---|---|---|---|
| | found | C 69.54% | H 6.60% |

Determination of the molecular weight by gel permeation chromatography in tetrahydrofuran solution using Ultrastyragel ® columns (from water Assoc., Milford, USA) having pore values of 1,000, 500 and 100 Å gave a number average $\overline{M}_n$ of 1,060 and a weight average $\overline{M}_w$ of 2,010.

In an analogous manner, benzil dimethyl ketal is reacted with the following diols or mixtures of alcohols in the molar ratio given:

| P1 No. | Equivalents of diol (per equivalent of BDMC) | | Ratio A:D:M according to NMR spectrum | Analysis | | | |
|---|---|---|---|---|---|---|---|
| | | | | % C | % H | $\bar{M}_n$ | $\bar{M}_w$ |
| 2 | 0.8 | triethylene glycol | 20:16:9 | 70.82 | 6.68 | 960 | 2120 |
| 3 | 1.25 | triethylene glycol | 8:10:1 | 67.84 | 6.87 | 1020 | 1840 |
| 4 | 0.55 | triethylene glycol | 7:4:6 | 72.53 | 6.49 | 560 | 1080 |
| 5 | 1 | diethylene glycol | 6:6:1 | 72.15 | 6.29 | 730 | 1970 |
| 6 | 1 | polyethylene glycol 400 | 8:8:1 | 63.39 | 7.51 | 2560 | 9080 |
| 7 | 1 | polyethylene glycol 600 | 5:5:1 | 61.10 | 7.91 | 3200 | 9150 |
| 8 | 1 | polyethylene glycol 1000 | 3:3:1 | 57.71 | 8.27 | 2270 | 5870 |
| 9 | 1 | polytetramethylene glycol 650 | 8:8:1 | 70.03 | 9.40 | 6000 | 21400 |
| 10 | 1 | hexane-1,6-diol | 8:8:1 | 77.22 | 7.31 | 1470 | 3490 |
| 11 | 1 | hydroquinone-bis(2-hydroxyethyl) ether | 5:5:1 | 73.24 | 5.97 | 1350 | 3170 |
| 12 | 1 | polypropylene glycol 400 | 4:4:3 | 67.19 | 8.52 | 640 | 1530 |
| 13 | 1 | polypropylene glycol 425 | 1:1:1 | 67.05 | 8.69 | 720 | 1520 |
| 14 | 1 | polypropylene glycol 750 | 1:1:1 | 64.90 | 9.22 | 850 | 1940 |
| 15 | 1 | polypropylene glycol 1200 | 1:1:1 | 63.77 | 9.63 | 660 | 2200 |
| 16 | 1 | polyethylene glycol 200 | 4:4:1 | 67.51 | 6.98 | 1190 | 2720 |
| 17 | 1 | polyethylene glycol 300 | 3:3:1 | 64.30 | 7.42 | 1400 | 3060 |
| 18 | 0.8 | hexane-1,6-diol | 20:16:9 | 76.76 | 6.92 | 1010 | 2240 |
| 19 | 1 | 1,4-bis(hydroxymethyl)-cyclohexane | 3:3:1 | 77.75 | 7.24 | 686 | 1191 |
| 20 | 0.5 / 0.5 | triethylene glycol and hexane-1,6-diol | 3:3:1 | 73.45 | 7.06 | 1015 | 2389 |
| 21 | 0.8 / 0.2 | triethylene glycol and N-methyldiethanolamine | 5:5:2 | 69.61 | 6.68 | 744 | 1330 |
| 22 | 1 | N-methyldiethanolamine | 3:4:1 | 67.53 | 7.41 | 291 | 318 |
| 23 | 0.80 / 0.133 | triethylene glycol and triethanolamine | 15:14:6 | 69.01 | 6.66 | 507 | 693 |
| 24 | 0.867 / 0.133 | triethylene glycol and triethanolamine | 3:3:1 | 69.67 | 6.77 | 514 | 724 |
| 25 | 0.80 / 0.133 | triethylene glycol and tris(2-hydroxyethyl) isocyanurate | 15:14:4 | 68.80 | 6.40 | 1098 | 2542 |
| 26 | 1 | tris(2-hydroxyethyl) isocyanurate | 4:3:2 | 58.71 | 6.75 | 1026 | 1908 |

USE EXAMPLES:

(a) in polyester resin 99.5 parts of an unsaturated polyester resin (Roskydal® UV502A, from Bayer AG) dissolved in styrene are mixed with 0.5 parts of a flow-improving agent (Byketol(R) 300, from Byk-Mallinckrodt) and 2 parts of the polyketal photoinitiator listed in the Table, while heating to 40–50° C.

To test the curing speed (reactivity), samples having a layer thickness of 100 μm are spread on white cardboard and are exposed in a PPG irradiator to 2 mercury medium-pressure lamps, 80 W/cm each. The sample is run through the instrument at a belt velocity of 10 m/min as many times as necessary until the surface is dry to the touch. The number of runs required is a measure of the reactivity of the resin. The fewer the number of runs needed, the more reactive the sample.

To determine the degree of curing, samples having a layer thickness of 100 μm are spread onto glass plates and exposed in three runs at 10 m/min in a PPG irradiator. After 30 minutes, the pendulum hardness of the cured film is determined by the method of König (DIN 53 157). This is a measure of the degree of curing of the film.

The odour occurring during the exposure of the samples is judged on a scale from 1 to 5. 1 denotes complete absence of odour and 5 denotes a very unpleasant odour.

| Photoinitiator No. | Runs until dry to the touch | Pendulum hardness (sec.) after 3 runs | Odour |
|---|---|---|---|
| 1 | 2 | 132 | 2 |
| 2 | 1 | 126 | 1–2 |
| 3 | 2 | 122 | 1–2 |
| 4 | 1 | 131 | 1–2 |
| 5 | 1 | 136 | 1–2 |
| 6 | 2 | 113 | 2 |
| 7 | 2 | 83 | 2 |
| 10 | 2 | 136 | 2 |
| 11 | 2 | 133 | 2 |
| 12 | 2 | 94 | 2 |
| 13 | 2 | 80 | 2 |
| 16 | 2 | 131 | 2 |
| 17 | 2 | 123 | 2 |
| 18 | 2 | 139 | 2 |
| 19 | 2 | 148 | 2 |
| 20 | 2 | 144 | 3 |
| 21 | 2 | 139 | 3 |
| 22 | 2 | 138 | 3 |
| 24 | 2 | 138 | 3 |
| 25 | 2 | 142 | 3 |
| 26 | 2 | 126 | 2 |

(b) in acrylate resin 69 parts of an epoxy acrylate (Ebecryl® 608, UCB), 30 parts of an oligomeric triacrylate (OTA 480, UCB) and 1 pair of a silicone diacrylate (Ebecryl® 350, UCB) are mixed and 2 parts of the polyketal photoinitiator listed in the Table are dissolved in this mixture with heating to about 50° C.

White carboards are coated by means of a 6 μm doctor blade with the resin samples and are irradiated at different running speeds in a PPG irradiator by 2 UV lamps of 80 W/cm each. The highest speed at which a surface dry to the touch is obtained is a run is listed as the cure speed and is a measure of the reactivity of the initiator.

In addition, glass plates are coated by means of 100 μm doctor blade with the samples and are cured in a run at a speed of 10 m/min in the PPG irradiator. The pendulum hardness of these samples is determined by the method of König (DIN 53 157), which represents a measure of the degree of curing of the resin achieved.

| Photoinitiator No. | Curing speed (m/min) | Pendulum hardness (sec) |
|---|---|---|
| 2 | 5 | 132 |
| 6 | 4 | 88 |
| 7 | 2.8 | 66 |
| 11 | 4 | 92 |
| 12 | 3.3 | 85 |
| 16 | 5 | 153 |
| 18 | 5 | 146 |
| 19 | 5 | 153 |
| 20 | 5 | 148 |

What is claimed is:

1. A compound or mixture of compounds of the formula I

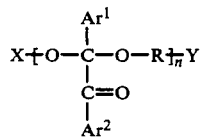

in which X is a group $R^1$ or HO—R—, Y is a group —OH or

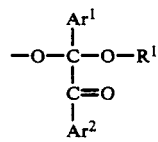

n is 2-20, $Ar^1$ and $Ar^2$ independently of one another are phenyl, tolyl, chlorophenyl or bromophenyl, R is a polymethylene radical having 4-30 C atoms which can be interrupted once or several times by —O—, —S—, —N($R^2$)— or a group

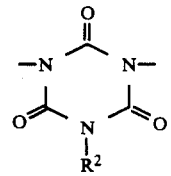

and which can be mono- or polysubstituted by $C_1$–$C_4$alkyl, cyclohexyl, phenyl, halogen, $C_1$–$C_4$alkoxy, phenoxy, $C_7$–$C_9$-phenylalkyl, $C_2$–$C_8$dialkylamino, morpholino or piperidino, $R^1$ is methyl or ethyl, $R^2$ is hydrogen, $C_1$–$C_4$alkyl, cyclohexyl, phenyl, tolyl, benzyl, acetyl, benzoyl or is a group —$CH_2CH_2R^6$ or —$SO_2$—$R^5$ is $C_1$–$C_{12}$alkyl, phenyl or $C_7$–$C_{18}$alkylphenyl, $R^6$ is hydroxy or —OC($Ar^1$)(CO—$Ar^2$)—O—$R_{1-5}$Y.

2. A compound or a mixture of compounds according to claim 1 of the formula I, in which n is 2-10, $Ar^1$ and $Ar^2$ are phenyl, R is either a —($CH_2$)$_m$— radical having an m of 5-10 or is a —($CH_2CH_2O$)$_p$$CH_2CH_2$— radical $R^2$ is $C_1$–$C_4$alkyl, cyclohexyl, phenyl or benzyl and X and Y are as defined in claim 1.

3. A compound or a mixture of compounds according to claim 1 of the formula I, in which n is 2-10, $Ar^1$ and $Ar^2$ are phenyl, R is a —($CH_2CH_2O$)$_p$—$CH_2CH_2$— radical having a p of 1-10 or is a —($CH_2$)$_6$— radical, $R^1$ is methyl and X and Y are as defined in claim 1.

* * * * *